United States Patent
Ornberg et al.

(10) Patent No.: US 9,232,889 B2
(45) Date of Patent: Jan. 12, 2016

(54) METHOD AND APPARATUS FOR OCULAR SURFACE IMAGING

(75) Inventors: Richard L. Ornberg, Burleson, TX (US); Gary W. Williams, Burleson, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 19 days.

(21) Appl. No.: 12/704,083

(22) Filed: Feb. 11, 2010

(65) Prior Publication Data

US 2010/0204584 A1     Aug. 12, 2010

Related U.S. Application Data

(60) Provisional application No. 61/151,880, filed on Feb. 12, 2009.

(51) Int. Cl.
| | |
|---|---|
| A61B 6/00 | (2006.01) |
| A61B 3/10 | (2006.01) |
| A61B 5/00 | (2006.01) |
| G06T 7/00 | (2006.01) |

(52) U.S. Cl.
CPC .............. *A61B 3/101* (2013.01); *A61B 5/0059* (2013.01); *G06T 7/0012* (2013.01); *G06T 2207/10012* (2013.01); *G06T 2207/10056* (2013.01); *G06T 2207/10064* (2013.01); *G06T 2207/30041* (2013.01)

(58) Field of Classification Search
CPC .............. A61B 5/0059; A61B 1/0646; A61B 1/00186; A61B 5/0071; A61B 5/0075; A61B 1/043; A61B 1/00096; A61B 3/12

USPC .......................................... 600/407, 467–478
See application file for complete search history.

(56) References Cited

U.S. PATENT DOCUMENTS

| | | | |
|---|---|---|---|
| 5,852,498 | A | 12/1998 | Youvan et al. |
| 5,986,271 | A | 11/1999 | Lazarev et al. |
| 5,988,271 | A | 11/1999 | Oneal et al. |
| 6,006,756 | A | 12/1999 | Shadduck |
| 6,044,196 | A | 3/2000 | Winston et al. |
| 6,049,367 | A | 4/2000 | Sharp et al. |
| 6,252,979 | B1 * | 6/2001 | Lee et al. .................... 382/133 |
| 6,299,305 | B1 | 10/2001 | Miwa |
| 7,860,286 | B2 | 12/2010 | Wang et al. |
| 7,889,948 | B2 | 2/2011 | Steedly et al. |
| 8,292,878 | B2 | 10/2012 | Arnoldussen et al. |
| 2002/0151774 | A1 | 10/2002 | Soller et al. |

(Continued)

FOREIGN PATENT DOCUMENTS

| | | |
|---|---|---|
| CN | 1833257 A | 9/2006 |
| EP | 2172150 | 7/2010 |

(Continued)

OTHER PUBLICATIONS

International Search Report corresponding to PCT Application Serial No. PCT/US2010/023865 dated Apr. 7, 2010.
Written Opinion corresponding to PCT Application Serial No. PCT/US2010/023865 dated Apr. 7, 2010.

(Continued)

*Primary Examiner* — Mark Remaly
(74) *Attorney, Agent, or Firm* — Haynes and Boone, LLP

(57) ABSTRACT

The invention provides apparatuses and methods for detecting corneal surface defects. The methods and/or an apparatus of the invention can be used to detect corneal surface diseases, such as dry eye.

19 Claims, 7 Drawing Sheets

(56) References Cited

U.S. PATENT DOCUMENTS

| | | | |
|---|---|---|---|
| 2003/0163049 A1* | 8/2003 | Balas | 600/476 |
| 2005/0105788 A1 | 5/2005 | Turek et al. | |
| 2005/0134796 A1* | 6/2005 | Zelvin et al. | 351/206 |
| 2006/0077581 A1 | 4/2006 | Schwiegerling et al. | |
| 2006/0099714 A1* | 5/2006 | Mata et al. | 436/106 |
| 2006/0142662 A1 | 6/2006 | Van Beek | |
| 2006/0274269 A1 | 12/2006 | Koest | |
| 2007/0046778 A1 | 3/2007 | Ishihara et al. | |
| 2008/0077581 A1 | 3/2008 | Drayer et al. | |
| 2008/0086048 A1 | 4/2008 | Dupps, Jr. et al. | |
| 2008/0090198 A1 | 4/2008 | Liang et al. | |
| 2008/0239070 A1 | 10/2008 | Westwick et al. | |
| 2009/0153798 A1 | 6/2009 | Dick et al. | |
| 2010/0004537 A1 | 1/2010 | Eilers et al. | |
| 2010/0004538 A1 | 1/2010 | Eilers et al. | |
| 2010/0079580 A1 | 4/2010 | Waring, IV | |
| 2010/0128960 A1 | 5/2010 | Yumikake | |
| 2011/0164218 A1 | 7/2011 | Ornberg | |
| 2011/0200242 A1 | 8/2011 | Takama et al. | |
| 2011/0202044 A1 | 8/2011 | Goldshleger et al. | |
| 2011/0262891 A1 | 10/2011 | Ozaki et al. | |
| 2011/0274322 A1 | 11/2011 | Kern | |

FOREIGN PATENT DOCUMENTS

| | | |
|---|---|---|
| JP | 07-039519 | 10/1995 |
| JP | 2000-237135 | 5/2000 |
| JP | 2000-296109 | 10/2000 |
| JP | 2007-090044 | 12/2007 |
| JP | 2008-264137 | 11/2008 |
| JP | 2009-502220 | 1/2009 |
| WO | WO 2010/039206 A1 | 4/2010 |
| WO | WO2010/093772 | 8/2010 |
| WO | WO 2011/139837 | 10/2011 |

OTHER PUBLICATIONS

Begley et al.; "Effect of lens care systems on corneal fluorescein staining and subjective comfort in hydrogel lens wearers"; Clinical Article: ICLC; vol. 21; pp. 7-13 (Jan./Feb. 1994).

Bron et al.; "Grading of corneal and conjunctival staining in the context of other dry eye tests"; Cornea; Clinical Sciences; vol. 22; No. 7; pp. 640-650 (Oct. 2003).

Dean et al.; "Clinical Technique; Documentation of corneal epithelial defects with fluorescein-enhanced digital fundus camera photography"; Clinical and Experimental Ophthalmology; vol. 36; pp. 113-118 (2008).

Lemp; "Report of the National Eye Institute/Industry Workshop on Clinical Trials in Dry Eyes"; CLAO; vol. 21, No. 4; pp. 221-232 (Oct. 1995).

Novitskaya et al.; "A novel method to study fluorescein staining of the ocular surface using the fluorescein angiogram setting of the fundus camera"; Contact Lens & Anterior Eye; vol. 30; pp. 258-259 (2007).

Saari, K. Matti: "Immunology of the lacrimal gland, tear film and ocular surface;" Book Review, Graefe's Archive of Clinical Experimental Ophthalmology; vol. 245; p. 471 (2007).

Stachs, Oliver, et al., "In vivo three-dimensional confocal laser scanning microscopy of the epithelial nerve structure in the human cornea," Laboratory Investigation; Graefe's Archive for Clinical Experimental Ophthalmology; vol. 245, No. 4, Mar. 20, 2007; pp. 569-575, XP55004942, ISSN: 0721-832X, DOI: 10.1007/s00417-006-0387-2, figures 1-5.

European Patent Office, International Search Report and Written Opinion dated Aug. 26, 2011, Application No. PCT/US2011/034304, 15 pages.

* cited by examiner

METHOD AND APPARATUS FOR OCULAR SURFACE IMAGING

CROSS-REFERENCE TO RELATED APPLICATION

This application claims priority under 35 U.S.C. §119 to U.S. Provisional Patent Application No. 61/151,880 filed Feb. 12, 2009, the entire contents of which are incorporated herein by reference.

FIELD OF THE INVENTION

The invention relates to apparatuses and methods for detecting corneal surface defects. An apparatus and method of the invention can be used to detect corneal surface diseases, such as dry eye.

BACKGROUND OF THE INVENTION

The diagnosis and prognosis of ocular surface diseases, such as keratoconjunctivitis sicca (dry eye), involves several tests. One of the tests includes staining the ocular surface with a dye, followed by visual examination for stained surface defects. Lesions in the epithelial cell layers of the cornea adsorb stain and allow for the penetration of stain into interstitial spaces. The resultant bright speckled appearance of the otherwise black cornea is a hallmark pathology of cornea disease. Visual examination has been used since the early 1900s as a diagnostic for surface eye disease. However, the variability and reliability of these assessments has been poor when performed by individual physicians. Hence there is an urgent need for a consistent measure of surface staining that is free of human bias and error. Heretofore, quantitative image analysis of ocular surface images has proven difficult for at least three reasons.

The first reason relates to Purkinje images of the illumination source in the images of the cornea and conjunctiva. The Purkinje image invariably interferes with image analysis and feature detection. Since it is not constant from one image to the next, such specular images are impossible to control for and must be removed prior to image analysis. Spectral methods are routinely used in fluorescence microscopy and whole body imaging to block undesired reflected light. Novitskaya et al. and Dean et al. described the use of a retinal camera having filtering properties for ocular surface stain imaging (Novitskaya et al., 2007, *Contact Lens & Anterior Eye* 30:258-259; Dean et al., 2008, *Clinical and Experimental Ophthalmology* 36:113-118). Novitskaya et al. and Dean et al. used digital fundus camera equipped with two filters, a blue exciter filter and a green bandpass filter, to detect fluorescence emitted from a fluorescein stained cornea. The fundus camera is designed to image fluorescein injected in to the vasculature as a means to assess retinal blood flow. The spectral properties of these filters were not described.

A second difficulty in accurately detecting and measuring corneal stain relates to the methods used to capture corneal images. Any object in an image that is to be measured has to be in sharp focus in order to visually or mathematically delineate the boundaries of the object. Stained objects on the corneal surface reside on a highly curved surface and require the use of methods that increase the depth of focus or depth of field in the image. The average height of the cornea from the limbal edge to the apex, also called the sag height is 2.8 millimeters for the human eye. The standard of care diagnostic system for viewing and imaging the cornea uses a biomicroscope on a slit lamp that has a depth of field of 0.7-0.8 mm on average. Hence any given stained corneal image from such a system can not possibly have all stained objects in sharp focus for subsequent analysis. Other imaging systems such as the retinal camera described by Novitskaya et al. and Dean et al. have a similar narrow depth of field for adequate image capture of the stained cornea.

A third difficulty in accurately detecting and measuring corneal stain relates to the methods used to separate surface stained objects from surrounding image elements for subsequent measurement. Images of stained ocular surfaces from patients with dry eye or other ocular surface diseases generally have bright punctate stained objects of interest amidst a background fluorescence that is an unwanted signal and is not to be included in the measurement.

Consequently, there is a need in the art to eliminate unwanted specular images in corneal staining and to capture full field in focus images of the corneal surface while enhancing a light signal that represents ocular surface defects for accurate diagnosis and monitoring of corneal surface diseases.

SUMMARY OF THE INVENTION

The invention provides methods of detecting ocular surface diseases, the methods comprising: (a) illuminating the ocular surface of an eye of a patient with a light from a light source, wherein the light is transmitted in a first predetermined wavelength range by an illumination filter positioned between the light source and the ocular surface, and wherein the light in the first predetermined wavelength range excites a contrast agent bound to defects on the ocular surface; and (b) detecting a light signal emitted from the contrast agent, wherein the light signal is transmitted in a second predetermined wavelength range by an imaging filter to an image capture device, wherein the imaging filter is positioned between the ocular surface and the image capture device. In one aspect, the image capture device comprises an optical system with appropriate optics to increase depth of field in the image and transmits full field in focus image signals to a machine readable storage medium comprising instructions that provide quantitative analysis of contrast agent intensity and distribution.

The invention further provides methods of detecting an ocular surface disease, the method comprising: (a) illuminating the ocular surface of an eye of a patient with a light from a light source, wherein the light is polarized in a first orientation by an illumination filter positioned between the light source and the ocular surface, and wherein the light polarized in the first orientation excites a contrast agent bound to defects on the ocular surface; and (b) detecting a light signal emitted from the contrast agent, wherein the light signal is polarized in a second orientation by an imaging filter, and is transmitted by the imaging filter to an image capture device, wherein the imaging filter is positioned between the ocular surface and the image capture device. In one aspect, the image capture device comprises an optical system with appropriate optics to increase depth of field in the image and transmits full field in focus image signals to a machine readable storage medium comprising instructions that provide quantitative analysis of contrast agent intensity and distribution in an automated fashion such that there is little or no human intervention in obtaining contrast agent distribution data.

In certain aspects, the contrast agent can be a fluorescent dye, a colored dye, or a natural substance, such as blood.

In yet another aspect, the first filter and the second filter are polar filters, and are adjusted in opposite directions.

The invention also provides an ocular surface examination apparatus, comprising: (a) a light source; (b) an illumination means for directing light along an illumination path onto an ocular surface; (c) an imaging means for directing reflected light from the ocular surface of a patient along an imaging path to enable an image of the ocular surface to be viewed; (d) an illumination filter that transmits light in the illumination path; and (e) an imaging filter that transmits reflected light in the imaging path, wherein the light in the illumination path can pass through the first filter, but cannot pass through the second filter.

The invention also provides an ocular surface examination apparatus, comprising: (a) a light source for directing light along an illumination path onto an ocular surface; (b) an illumination filter that transmits light in the illumination path; (c) an imaging filter that transmits light reflected from a contrast agent on the ocular surface of a patient along an imaging path; and (d) an image capture device for detecting light reflected from the contrast agent on the ocular surface of the patient; wherein the light in the illumination path cannot pass through the imaging filter.

Specific preferred embodiments of the invention will become evident from the following more detailed description of certain preferred embodiments and the claims.

DETAILED DESCRIPTION

The invention relates to methods and apparatuses that can be used to quantitatively measure corneal staining. In particular, a method and apparatus of the invention can be used to capture images of a stained ocular surface (i.e. cornea) for the generation of objective information about ocular surface staining. The methods of the invention can be used, for example, as a diagnostic for ocular surface disease, such as dry eye, Sjogren's disease, infectious disease and contact lens wear problems, to measure therapeutic efficacy in clinical trials, or to measure efficacy of potential therapeutics in animal models of ocular surface diseases, such as dry eye.

Figure 1:
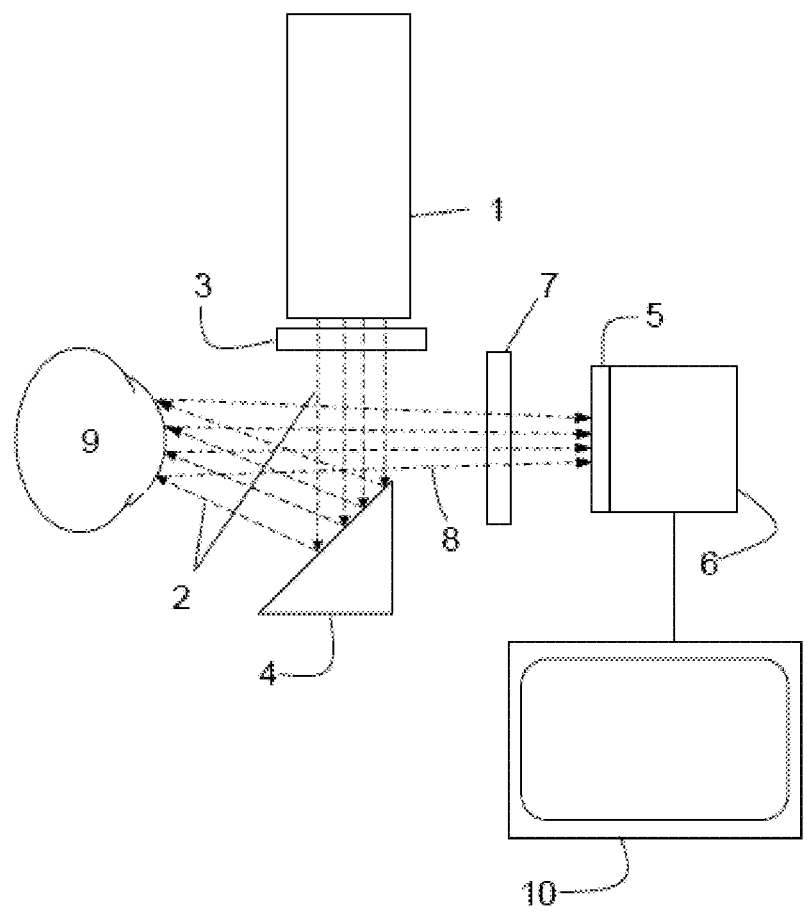
FIG. 1 is a schematic diagram showing a configuration of an ophthalmic apparatus of the invention, wherein light in the illumination path 2 is reflected toward the ocular surface of an eye 9 via a half-mirror 4.
Figure 2:
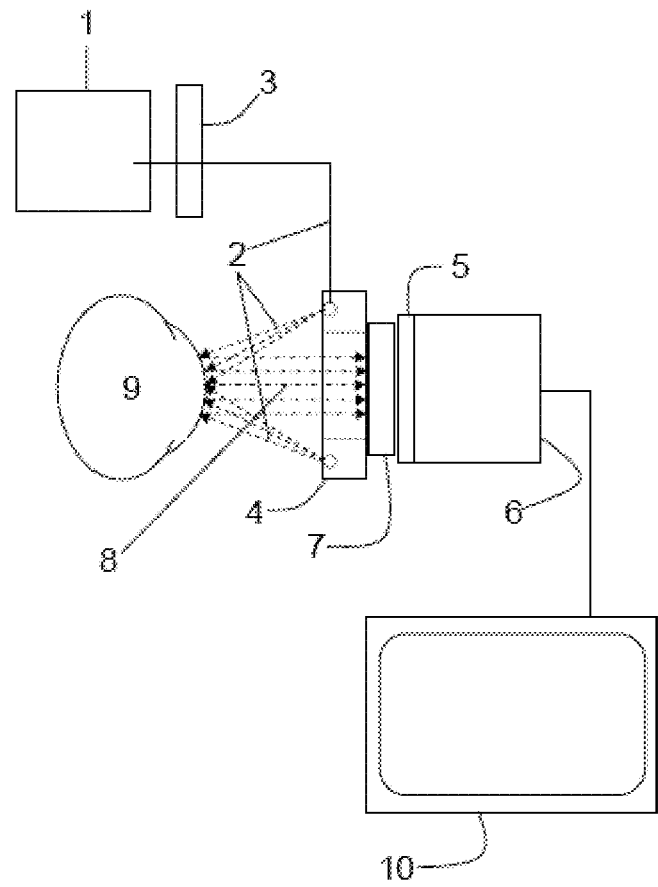
FIG. 2 a schematic diagram showing a configuration of an ophthalmic apparatus of the invention, wherein light in the illumination path 2 is directed toward the ocular surface of an eye 9 via a ring light 4.

Exemplary configurations of an apparatus of the invention are shown in FIG. 1 and FIG. 2, and are discussed in detail below.

In certain embodiments, a method and/or apparatus of the invention comprises illuminating an ocular surface with a light that is filtered at a predetermined wavelength or polar orientation. The light travels along an illumination path toward the ocular surface, which comprises a contrast agent that can be excited by the light beam emitted from a light source. The light signal emitted from the contrast agent travels along an imaging path toward an image capture device, such as a camera. Cameras can be of several types including digital single lens reflex cameras with RGB CMOS sensors or black and white CCD cameras. In a particular embodiment, the light signal captured by the image capture device is either spectrally isolated from the light in the illumination path, or has an opposite polar orientation relative to the light in the illumination path, as discussed in more detail below.

A suitable contrast agent that can be used in a method and/or apparatus of the invention is any agent that can bind to a defect on the ocular surface and be detected by specific light absorption and emission characteristics (i.e. color or fluorescence emission). For example, fluorescein, lissamine green, rose bengal have been used to measure surface irritation associated with dry eye (Bron et al, 2003, *Cornea* 22:640-650) and contact lens wear (Begley et al, 1994, *Int Contact Lens Clin* 21:7-13.). A contrast agent can be administered to a patient via an eye drop, for example, aqueous solutions of sodium fluorescein or lissamine green are typically instilled as a one to five microliter drop onto the surface of the eye.

Alternatively, a contrast agent can be administered from a dye impregnated strip, such as sodium fluorescein impregnated strip (Fluorets™; Chauvin Pharmaceuticals, Essex, United Kingdom), in which a wetted strip is placed in contact with the eye at the lower lid margin for a period of a few minutes.

As used herein, a "patient" can be any mammal. Preferably, the patient is a human, monkey, rabbit, mouse, or rat. Most preferably, the patient is a human.

FIG. 1 provides a schematic diagram showing one configuration of an ophthalmic apparatus of the invention.

Referring to FIG. 1, a light source 1 emits light in an illumination path 2 toward a half-mirror 4. The light in the illumination path 2 passes through an illumination filter 3, then contacts the half-mirror 4, and is reflected toward the surface of an eye 9. The light in the illumination path 2 is adapted to excite a contrast agent present on the surface of the eye. A light signal emitted from the excited contrast agent travels in an imaging path 8 toward a lens 5. An imaging filter 7 is positioned in the imaging path 8 between the ocular surface of the eye 9 and the lens 5.

Images of corneal surface defects are captured by an image capture device 6 and transmitted to a machine readable storage medium 10. The machine readable storage medium 10 comprises instructions for providing quantitative analysis of contrast agent intensity and distribution. Images of corneal surface defects can be visualized via a display unit, such as a monitor, that is connected to the machine readable storage medium 10.

FIG. 2 shows a schematic diagram showing another configuration of an ophthalmic apparatus of the invention.

Referring to FIG. 2, a light source 1 emits light in an illumination path 2 toward an illumination device 4. The illumination device can be, for example, a fiber optic ring light. The light in the illumination path 2 passes through an illumination filter 3, then contacts the illumination device 4, which transmits the light toward the surface of an eye 9. The light in the illumination path 2 is adapted to excite a contrast agent present on the surface of the eye. Light emitted from the excited contrast agent travels in an imaging path 8 toward a lens 5. An imaging filter 7 is positioned in the imaging path 8 between the ocular surface of the eye 9 and the lens 5.

Images of corneal surface defects are captured by an image capture device 6 and transmitted to a machine readable storage medium 10. The machine readable storage medium 10 comprises instructions for providing quantitative analysis of contrast agent intensity and distribution. Images of corneal surface defects can be visualized via a display unit, such as a monitor, that is connected to the machine readable storage medium 10.

In certain embodiments, illumination of the ocular surface using a method and/or apparatus of the invention is accomplished with light having specific wavelength ranges and/or polarized light, and images of the ocular surface are captured at specific wavelength ranges and/or polarization to produce images that are free of specular images of the illumination system.

In one embodiment, the wavelength range of light used to illuminate the ocular surface is spectrally isolated from the light used to capture the images (i.e. the light in the illumination path 2 cannot pass through the filter 7 in the imaging path 8). Spectral isolation of the light in an illumination path 2 from that in the imaging path 8 can be accomplished, for example, using a set of bandpass filters, one filter for illumination and a different filter for image capture. The wavelength range of the two filters cannot overlap, and therefore have very large out-of-band optical densities. Consequently, no light from the light source 1 can pass into the image capture device 6 and be imaged. For example, where fluorescein is a contrast agent on the ocular surface of the eye 9, a method and/or apparatus of the invention can comprise an illumination filter 3 that can transmit light in a range of 465-500 nanometers, for optimum excitation of fluorescein, and an imaging filter 7 that can transmit light greater than 515 nanometers, for optimum detection of fluorescein. Depending on the spectral properties of the contrast agent, other wavelength ranges for absorption and detection would be preferred. The optical density for each filter outside of these ranges would be at least 5.0 (i.e., transmittance greater than or equal to 0.000001).

In another embodiment, a method and/or apparatus of the invention comprises polarized light to illuminate the ocular surface, wherein the illumination filter 3 and the imaging filter 7 are polar filters. For example, the ocular surface of an eye is illuminated with circularly polarized light, using an illumination filter 3 that is a left or right circular polar filter, and the imaging filter 7 is a right or left circular polar filter, respectively (i.e. where the illumination filter 3 is a left circular polar filter, the imaging filter 7 is a right circular polar filter). Alternatively, the ocular surface of an eye is illuminated with plane polarized light, wherein the illumination filter 3 and imaging filter 7 are adjusted in opposite directions.

The arrangement (i.e. the illumination filter and the imaging filter are in different light paths) and properties of the filters in an apparatus and/or method of the invention ensures that an accurate image of ocular surface defects is captured, wherein the image is free from illumination artifacts (e.g. specular or Purkinje images from the light source). For example, where the contrast agent is a fluorescent dye, the illumination filter can be selected to transmit light in a particular range of wavelengths capable of exciting the dye, while the imaging filter can be selected to transmit light at wavelengths that are outside the wavebands transmitted by the illumination filter. The imaging filter will transmit fluorescence from the dye while blocking fluorescence that is generated from other objects on the ocular surface. Thus, the only signal captured for analysis will be associated with defects on the ocular surface that are bound to the dye.

In certain embodiments, images of corneal surface defects are captured by an image capture device, where they are stored and/or transferred to a machine readable storage medium. The machine readable storage medium comprises a program of instructions stored thereon for causing an electrical processor to execute automated method steps for image analysis, which is performed using an adaptive threshold algorithm, in conjunction with the light filtering accomplished with the illumination filter and the imaging filter, to segment stained objects from digital images. The adaptive threshold method iteratively adjusts the segmentation threshold until the rate of change in the number of pixels in the segmented image has reached a predetermined level.

In other embodiments, an optical system can be used to increase depth of field in an image captured using a method or apparatus of the invention. For example, an "optical system" can be used to place an aperture in the optical imaging path that increases the depth of focus in the final image, or to adjust the focal plane of the imaging system such that several images collected at different focal planes are collected and electronically rendered into a single in-focus image of the ocular surface (e.g. extended depth of field rendering). In certain embodiments, the optical system can be incorporated into an image capture device. An image that has been adjusted using the optical system is transmitted as a full field, in-focus image to a machine readable storage medium that comprises instructions that provide automated, quantitative analysis of contrast agent intensity and distribution. Automated analysis eliminates the possibility of human error in obtaining and/or interpreting the contrast agent distribution data.

The isolation or segmentation of stained objects in corneas stained with a contrast agent for size position and intensity measurements is not obvious, despite the fact the stained objects can be more quickly visualized in properly filtered, in-focus images. Faint background fluorescence of residual stain in the tear film and autofluorescence from the cornea and surrounding conjunctiva require the use of image processing to highlight the stained spots. Fourier image processing methods are one of several means to enhance the appearance and subsequent threshold segmentation of image objects. In certain embodiments, a method and/or apparatus of the invention can comprise the use of Fourier bandpass filtering to enhance and aid subsequent stained object detection.

Fourier image processing is based on the work of the French mathematician Jean Baptiste Joseph Fourier, which postulates that any measurement in time and space can be expressed as an equation of sin and cosine functions or, to use the Euler formula, a series of complex exponentials summed over an infinite range of frequencies. The Fourier transform is the mathematical operation that transforms the original measure or signal into an expression of complex exponentials with a range of amplitude coefficients and frequency terms. An image, being a two dimensional array of intensity measurements, can also be transformed to two dimensional arrays of complex exponentials. This Fourier transformation is often referred to as a transformation from the spatial domain to the frequency domain. In the frequency domain, one can highlight specific structures and remove others for subsequent analysis by removing certain frequencies from the transform and then calculating the inverse transform. For example, in stained cornea images, the bright conjunctiva surrounding the cornea and the diffuse background fluorescence are represented by lower frequency terms in the transform while stained spots are represented by high frequency terms. By multiplying the transform of the original image with a filter that reduces the low frequency terms and performing an inverse transform on the product, an image is created that has reduced the diffuse background and conjunctival intensities while maintaining the stained spots.

Thus, in certain embodiments of the invention, a Fourier band pass filter can be used with a predetermined frequency space to remove low frequency components (i.e., very large objects or background) and highlight high frequency components that include small punctate objects. Examples of potential filters include, but are not limited to, Gaussian and Butterworth filters. Fourier filtering advantageously permits detection of punctate stained regions against a varying background of unbound stain in the tear film (see Example 2 below, which illustrates process and results of Fourier band pass filter for detecting stained objects on the ocular surface).

All references cited in this application are expressly incorporated by reference herein for any purpose.

Unless otherwise required by context, singular terms used herein shall include pluralities and plural terms shall include the singular.

EXAMPLES

The following examples, including the experiments conducted and results achieved are provided for illustrative purposes only and are not to be construed as limiting the invention.

Example 1

Spectral Filtering Removes Purkinje Images of the Illumination Source from Images of Specular Surfaces The ability to spectrally remove the specular or Purkinje image from ocular surface fluorescence images was demonstrated with an artificial cornea prepared from a hard contact lens. For this a hard contact lens made of polymethylmethacrylate was coated with green fluorescent beads, (Bangs Laboratories, Inc, Fishers, Ind.) to simulate stained spots on a curve corneal surface. The spectral properties of these beads were similar to fluorescein. The artificial cornea was position in front of a Nikon digital single lens reflex camera and illuminated with a fiber optic ring light mounted to the lens of the camera. The fiber optic ring illuminator was configured such that band pass filters could be used to spectrally define the light emanating from the ring. Images were collected through either a green bandpass filter optimized for fluorescein emission wavelengths, (532+/−45 nm) or no filter.

Figure 3A:
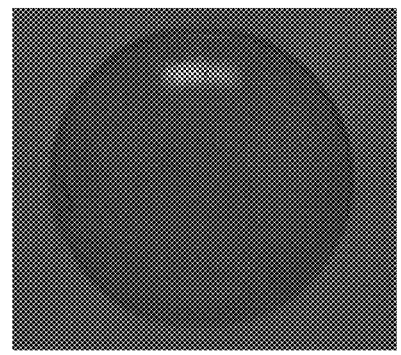
FIG. 3A shows an image of an artificial cornea obtained in ambient room light.
Figure 3B:
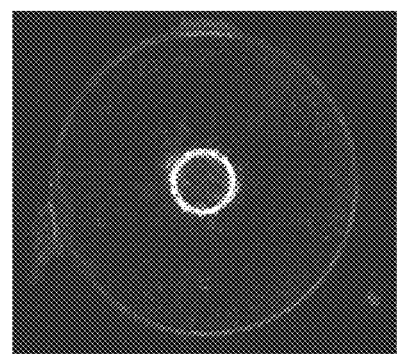
FIG. 3B shows an image of an artificial cornea obtained with white excitation light and 532AF45 fluorescein emission filter.
Figure 3C:
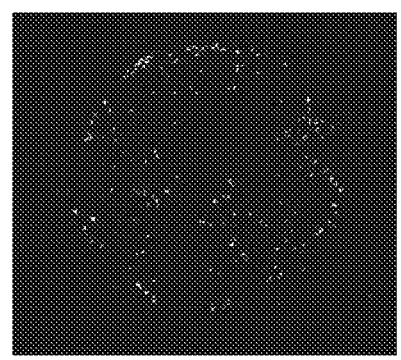
FIG. 3C shows an image of artificial cornea obtained with white excitation light and an HQ480/40 excitation filter in the illumination path.

The artificial cornea coated with fluorescent beads is shown in FIG. 3A illuminated with ambient white room light and imaged without a green blocking filter. A specular image of the dim room lamp was observed on the upper side of the lens surface. In FIG. 3B, the artificial cornea was illuminated with white light from a fiber optic ring light and an image was collected through the green bandpass filter. A bright specular image of the ring light was observed. In FIG. 3C, the artificial cornea was illuminated with filtered blue light, 480+/−40 nm; though the ring light and the images were collected with the green bandpass filter. The specular image of the ring was no longer observed and the fluorescent beads coating the surface became observable. The use of two filters, one for excitation and one for image collection, having non-overlapping wavelength ranges eliminated the specular image of the source illumination and allowed the beads to be more easily and consistently measured.

Example 2

Spectral Filtering Removes Purkinje Images of the Illumination Source from Images of the Ocular Surface A severe dry eye patient and a non-dry eye patient were subjected to corneal staining with 5 µL of 2% sodium fluorescein for 3 minutes, followed by a saline wash (Unisol 4 Saline Solution, Alcon Laboratories, Inc., Fort Worth, Tex.). The stained eyes were imaged with a Haag-Streit BX-900 slit lamp. The Haag-Streit slit lamp consisted of a stereo biomicroscope, a combination flash lamp and modeling lamp for illuminating the eye and a Canon 40D digital camera and computer for image capture. The slit lamp was modified by the addition of a fluorescein excitation bandpass filter to the flash lamp output and the insertion of a fluorescein emission filter in the light path to the between the eye and the camera. The fluorescein excitation filter had a bandpass (transmission>90%) of 483+/−32 nm and the emission filter had a bandpass of 536+/−40 nm. The out-of-band optical densities of these custom filters was designed to be ≥6, hence no excitation light passed into the camera.

Figure 4A:
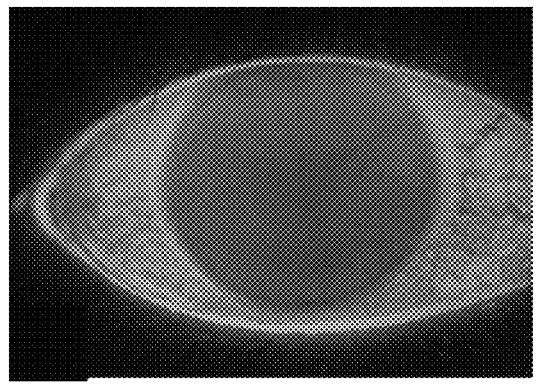
FIG. 4A shows an image of a cornea front a control, non-dry eye subject stained with 5 μL of 2% sodium fluorescein for 3 minutes, followed by a saline wash.
Figure 4B:
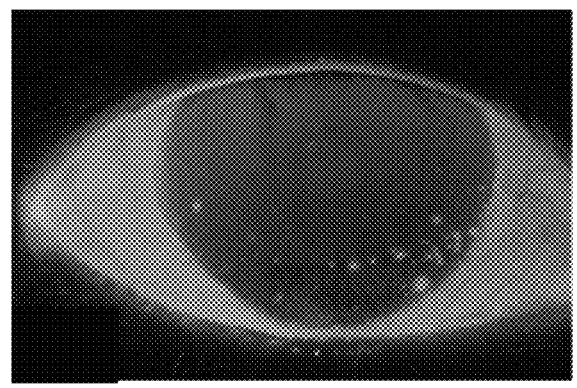
FIG. 4B shows an image of a cornea from a dry eye subject stained with 3 μL, of 2% sodium fluorescein for 3 minutes, followed by a saline wash.

As shown in FIG. 4, corneal images from the control non-dry eye subject (A) revealed a relatively uniform cornea with no obvious stained lesions, while from the dry eye subject (B) exhibited with several brightly stained punctate spots. The spots represented defects or lesions in the corneal epithelial layer associated with the dry eye condition. These images were suitable for quantifying the position, size, intensity and shape of the stained lesions. Again there were no Purkinje images of the illuminating source in these images.

Example 3

Fourier Analysis of Ocular Surface Defects of a Dry Eye Patient

Figure 5A:
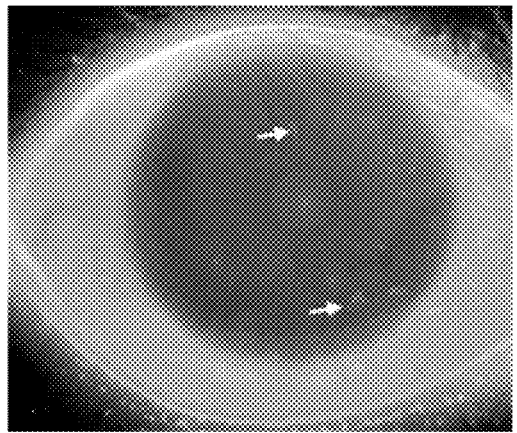
FIG. 5A shows an image of a cornea stained with fluorescein.
Figure 5B:
FIG. 5B shows an image of the fluorescein-stained cornea of FIG. 5A after image processing with a Fourier bandpass filter

The effect of the Fourier bandpass filtering process was illustrated in FIG. 5 and FIG. 6. The fluorescein corneal image in FIG. 5A was obtained with a camera based imaging system equipped with fluorescein spectral band pass filters as described above. The two dimensional Fourier transform of the image in FIG. 5A was then calculated using an unpadded fast Fourier transform algorithm found in most image analysis software. The transform was then multiplied by the Fourier transform of a low pass Gaussian filter and the inverse transform of the product was calculated to produce the image in FIG. 5B. As expected, the Fourier processing removed the low background brightness of the conjunctiva and background stain leading to an enhancement of the small speckled stained structures in the cornea (compare image in FIG. 5A and FIG. 5B).

Figure 6A:
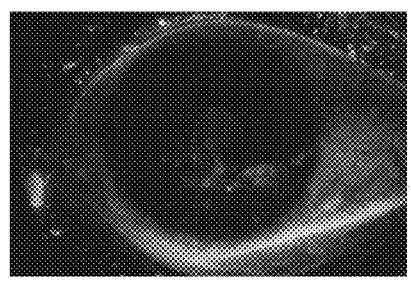
FIG. 6A shows an image of a corneal surface collected using spectral filtering to capture distribution of fluorescein staining.
Figure 6B:
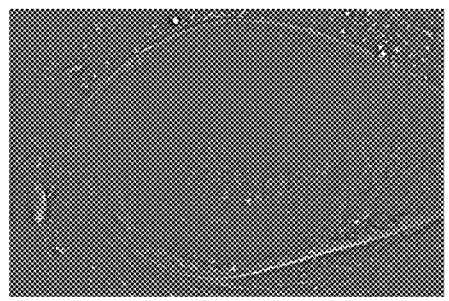
FIG. 6B shows the image from FIG. 6A filtered with Fourier bandpass filters.
Figure 6C:
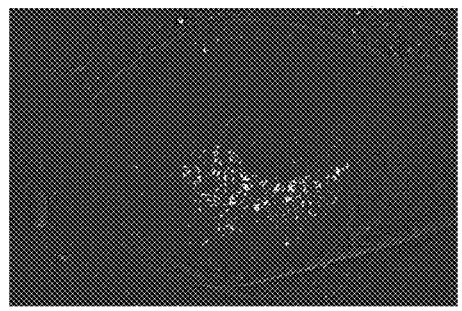
FIG. 6C shows threshold segmentation of the image from FIG. 6B.
Figure 6D:
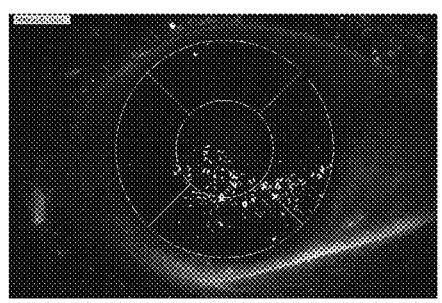
FIG. 6D shows a measurement grid often referred the NEI (National Eye Institute) grid overlaid on to FIG. 6A. The NEI grid is most often used to manually score corneal staining by direct observation through a slit lamp of imaging device.

The utility of the imaging method and the Fourier bandpass filtering process in measuring fluorescein stained objected in corneas is illustrated in FIG. 6A-D. As shown in FIG. 8A, the image collected using spectral filtering method captured the distribution of fluorescein staining on human cornea without Purkinje image of the lamp. The image in FIG. 6A was filtered using Fourier bandpass, to highlight fluorescein stained objects (FIG. 6B). Threshold segmentation of the image in FIG. 6B was performed, such that group pixels above a certain threshold intensity and size were isolated and overlaid in green. FIG. 6D shows detected objects illustrated in 6C along with a standard corneal scoring grid commonly referred to as the National Eye Institute (NEI) grid, recommended by the National Eye Institute for visually scoring staining use, (*Lemp M A. Report of the National Eye Institute/Industry workshop on Clinical Trials in Dry Eyes CLAO J.* 1995 October; 21 (4):221-32). These results demonstrated that Fourier processing allowed one to enhance contrast in an image based on the size of object, and was independent of the objects mean intensity when compared to threshold based methods. The methods were ideally suited to the cornea images and for fluorescein stained corneal defects in particular.

Example 4

Polar Filtering Eliminates Specular Images Reflecting from the Ocular Surface

The need to remove specular images of the illumination source from ocular surface images is not limited to fluorescein stained eyes. During the course of several other ocular examinations, such as measuring hyperemia or colored conjunctival stains, such as lissamine green or rose bengal, it would be advantageous to remove the specular images of the source to facilitate subsequent analysis. For non-fluorescent imaging, polarization optics can be used to filter specular reflected light from ocular images. An example of this is shown in FIG. 7

Figure 7A:
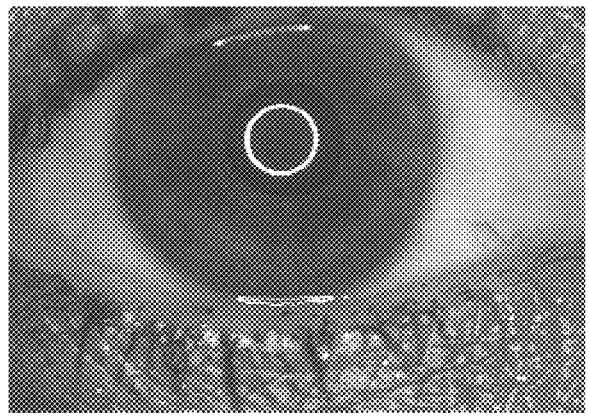
FIG. 7A shows an image of an ocular surface illuminated with left circularly polarized light.
Figure 7B:
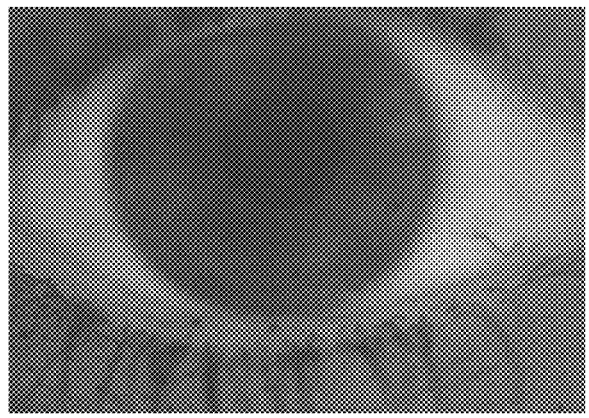
FIG. 7B shows an image of an ocular surface illuminated with left circular polarized light and imaged through a right circular polar filter.

FIG. 7A shows an image of an ocular surface obtained by illuminating with left circularly polarized light using a ring light source and imaged without a polar filter in the eye to camera light path. The specular image of the ring light appeared as a bright white ring in the center of the eye (FIG. 7A). FIG. 7B, shows an image of the ocular surface illuminated with left circular polarized light using the same ring light source and imaged through a right circular polar filter in the eye to camera light path. The specular reflected light from the ring light was blocked by the cross polar filter and the image was free of specular artifact (FIG. 7B). Thus, polarized light filtering eliminated the Purkinje artifacts from the ocular surface image.

It should be understood that the foregoing disclosure emphasizes certain specific embodiments of the invention and that all modifications or alternatives equivalent thereto are within the spirit and scope of the invention as set forth in the appended claims.

What is claimed is:

1. An ocular surface examination apparatus, comprising:
a light source for directing light along an illumination path onto an ocular surface;
an illumination filter that filters light in the illumination path prior to the light contacting the ocular surface, the illumination filter being structured to remain along the illumination path;
an imaging filter that filters light reflected from the ocular surface and transmits light from a contrast agent on the ocular surface of a patient along an imaging path, the imaging filter being structured to remain along the imaging path;
an image capture device for detecting light from the contrast agent on the ocular surface of the patient;
an optical system to increase depth of field by collecting several images from the image capture device at different focal planes and rendering the images into a single in-focus image;
wherein the illumination filter and the imaging filter are band-pass filters that transmit light in non-overlapping bands; and
a machine readable storage medium comprising a set of instructions that when executed by a processor, are configured to:
receive an image from the image capture device;
segment stained objects within the image to create a segmented image using a segmentation threshold; and
iteratively adjust the segmentation threshold until a rate of change in a number of pixels in the segmented image has reached a predetermined level;
wherein an optical density of the illumination filter at wavelengths other than 465 to 500 nm is at least 5.0 and an optical density of the imaging filter at wavelengths less than 515 nm is at least 5.0.

2. The apparatus of claim 1, wherein the optical system is configured to determine contrast agent intensity and distribution.

3. The apparatus of claim 1, wherein the illumination filter filters light to block light not in a first predetermined wavelength range, and the imaging filter filters light to block light not in a second predetermined wavelength range, wherein the first and second predetermined wavelength ranges do not overlap.

4. An ocular surface examination apparatus, comprising:
a light source for directing light along an illumination path onto an ocular surface;
an illumination filter that filters light in the illumination path prior to the light contacting the ocular surface, the illumination filter being structured to remain along the illumination path;
an imaging filter that filters light reflected from the ocular surface and transmits light from a contrast agent on the ocular surface of a patient along an imaging path, the imaging filter being structured to remain along the imaging path;
an image capture device for detecting light emitted from the contrast agent on the ocular surface of the patient;
an optical system to increase depth of field in the captured image; and
a machine readable storage medium comprising a set of instructions that when executed by a processor, are configured to:
receive an image from the image capture device;
segment stained objects within the image to create a segmented image using a segmentation threshold; and
iteratively adjust the segmentation threshold until a rate of change in a number of pixels in the segmented image has reached a predetermined level;
wherein the illumination filter and the imaging filter are band-pass filters that transmit light in non-overlapping bands, the illumination filter and the imaging filter being structurally positioned to continually prevent light from the light source from reaching the image capture device.

5. The apparatus of claim 4, wherein the captured image is free from Purkinje images.

6. The apparatus of claim 4, wherein the imaging filter passes light having a wavelength of about 536 nm.

7. The apparatus of claim 4, wherein optical density of the illumination filter at wavelengths other than 465 to 500 nm is at least 5.0 and optical density of the imaging filter at wavelengths less than 515 nm is at least 5.0.

8. The apparatus of claim 1, wherein the illumination filter is configured to filter light that does not have a wavelength in a range of 465 to 500 nm, and the imaging filter is configured to filter light having a wavelength less than 515 nm.

9. The apparatus of claim 1, wherein the illumination filter and the imaging filter are polar filters that are adjusted in opposite directions to each other.

10. The apparatus of claim 9, wherein the illumination filter and the imaging filter are circular polar filters in which one of the filters is a left circular filter and the other filter is a right circular filter.

11. The apparatus of claim 9, wherein the illumination filter and the imaging filter are plane polarized filters adjusted in opposite directions.

12. The apparatus of claim 4, wherein the illumination filter and the imaging filter are polar filters that are adjusted in opposite directions to each other.

13. The apparatus of claim 12, wherein the illumination filter and the imaging filter are circular polar filters in which one of the filters is a left circular filter and the other filter is a right circular filter.

14. The apparatus of claim 12, wherein the illumination filter and the imaging filter are plane polarized filters adjusted in opposite directions.

15. The apparatus of claim 4, wherein the illumination filter is configured to filter light that does not have a wavelength in a range of 465 to 500 nm, and the imaging filter is configured to filter light having a wavelength less than 515 nm.

16. An ocular surface examination apparatus, comprising:
a light source for directing light along an illumination path and through an illumination filter onto an ocular surface, the light source configured to excite a contrast agent on the ocular surface, the illumination filter being structured to remain along the illumination path;
an image capture device for detecting light emitted from the contrast agent;
an imaging filter positioned between the ocular surface and the image capture device, the imaging filter configured to filter light from the light source that is reflected from the ocular surface and to transmit light emitted from the contrast agent; and
a machine readable storage medium comprising a set of instructions that when executed by a processor, are configured to:
receive an image from the image capture device;
segment stained objects within the image to create a segmented image using a segmentation threshold; and
iteratively adjust the segmentation threshold until a rate of change in a number of pixels in the segmented image has reached a predetermined level;
wherein the illumination filter and the imaging filter are band-pass filters that transmit light in non-overlapping bands.

17. The apparatus of claim 16, wherein the illumination filter is configured to filter light that does not have a wavelength in a range of 465 to 500 nm, and the imaging filter is configured to filter light having a wavelength less than 515 nm.

18. The apparatus of claim 16, wherein the illumination filter and the imaging filter are polar filters that are adjusted in opposite directions to each other.

19. The apparatus of claim 12, wherein the illumination filter and the imaging filter are circular polar filters in which one of the filters is a left circular filter and the other filter is a right circular filter.

* * * * *